United States Patent [19]

Herring

[11] Patent Number: 4,988,516

[45] Date of Patent: Jan. 29, 1991

[54] INSECTICIDE

[76] Inventor: Sherry D. Herring, Rte. One Box 307, Slocomb, Ala. 36375

[21] Appl. No.: 226,513

[22] Filed: Aug. 1, 1988

Related U.S. Application Data

[63] Continuation of Ser. No. 841,180, Mar. 19, 1986, abandoned.

[51] Int. Cl.⁵ .................... A01N 25/00; A01N 59/14
[52] U.S. Cl. ........................................ 424/659; 424/84
[58] Field of Search .................... 424/84, 148, 659

[56] References Cited

U.S. PATENT DOCUMENTS 1,636,688  7/1927  Harris .................................. 424/148

FOREIGN PATENT DOCUMENTS

| 0067209 | 4/1984 | Japan | 424/148 |
| 0155305 | 9/1984 | Japan | 424/148 |
| 4654 | of 1899 | United Kingdom | 424/148 |

*Primary Examiner*—Allen J. Robinson
*Attorney, Agent, or Firm*—Fleit, Jacobson, Cohn, Price, Holman & Stern

[57] ABSTRACT

An insecticide comprised of a mixture of Boric Acid {ORTHOBORIC ACID U.S. Borax Co. EPA Reg. No. 1624-117}, white wheat flour, solid white vegetable shortening, onion white cane sugar, and water.

4 Claims, 1 Drawing Sheet

U.S. Patent     Jan. 29, 1991     Sheet 1 of 1     4,988,516
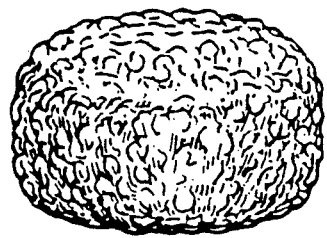

INSECTICIDE

This application is a continuation, of application Ser. No. 841,180, filed Mar. 19, 1986, now abandoned.

BACKGROUND OF THE INVENTION

1. Field of the Invention

The present invention relates to an insecticide for controlling insects such as cockroaches and to a method for preparing the insecticide.

2. Description of the Prior Art

It is well-known in the art to produce insecticides for treating cockroaches and other insects by utilizing boric acid as the active ingredient. For example, U.S. Pat Nos. 1,029,203 and 4,438,090 both disclose insecticides containing boric acid. Boric acid is used as the active ingredient because it is poisonous to the insect, and is relatively low in toxicity to human beings and animals such as house pets.

Accordingly, there have been many attempts made to incorporate boric acid into a composition. Typically, these compositions are placed in the area where the insects are located with the expectation that the insects will consume the composition, and therefore, the boric acid. Traditionally, the compositions take the form of tablets or powders. An example of such a product is Harris Roach Tablets TM.

It is scientifically recognized that roaches and other insects pre-taste their food, and in some cases can detect poisonous materials and will avoid the bait that contains the poison. In the above-described roach tablets, often what happens is that the roaches recognize the poison, and do not comsume the entire tablet. Thus, the tablets are not completely successful in exterminating the roaches or other insects.

Accordingly, it would be desirable to develop a composition such that the insects will consume significant portions of the entire composition and therefore the boric acid, so that the consumption will be fatal.

SUMMARY OF THE INVENTION

The present invention provides a novel composition which acts as an insecticide to exterminate roaches and other insects. The composition is characterized by using boric acid as the active ingredient and including the boric acid in a bait made up of white wheat flour, solid white vegetable shortening, chopped onions, white cane sugar and water. The ingredients are mixed in selected proportions to create a homogeneous mixture. The mixture is thereafter formed into patties which are placed in areas which are infested with insects. According to the present invention, the patties are effective for approximately one month.

It is an object of the present invention to produce a composition which acts as an insecticide to exterminate roaches and other insects such that the roaches will consume enough of the composition until it has ingested a fatal amount of boric acid.

It is another object of the present invention to incorporate the boric acid in a bait such that the insects do not detect the poisonous boric acid in the composition.

It is a further object of the present invention to develop a composition which takes the form of a patty which will allow the insects to comsume the composition in large amounts.

It is an additional object of the present invention to provide a patty which enables the odor of an attractant to be retained for long periods of time.

It is an additional object of the present invention to develop a composition which can be placed in areas which are insect infested, and is easily disposed of after it is no longer effective.

Other objects and features of the present invnetion will become apparent to those skilled in the art as the disclosure is made in the following description of a preferred embodiment of the present invention.

BRIEF DESCRIPTION OF THE DRAWINGS

The FIGURE is a representation of a patty used as an insecticide which embodies the teachings of the instant invention.

DETAILED DESCRIPTION OF THE INVENTION

The present invention is a method of preparing an insecticide comprised of 16 oz of boric acid and a bait comprised of 8 oz of white wheat flour, 4 oz of solid white vegetable shortening, 3 oz of chopped onion, 2 oz white cane sugar and 1 oz of water. The ingredients are then mixed to form a dough and then formed into patties 1½ in. in diameter and ½ in. in height as shown in the FIGURE. The patties are then placed in areas where roaches are known to live and feed. The patties may be used in areas of food preparation and near food products due to the low toxicity of this insecticide and the fact that the patties keep the insecticide from coming in contact with the food. The reason that this is an improvement and different from other insecticides containing boric acid is the ease of use of the patties and the fact that the roaches will eat this mixture and in fact prefer it to almost any other food.

By utilizing the onion, vegetable shortening, and water, the patties are inherently moist in nature. This moisture is necessary to provide the odor to attract the insects. Further, the soft moist patty allows the insects to eat the bait and boric acid in large amounts. Also, due to the presence of the onion, the insests can smell the bait from a distance away, unlike commonly used hard tablets which do not have as much of a food odor. Additionally, the insects can eat from the patties from several sides and have a large feeding area. This is advantageous because insects, such as roaches, are community eaters and like to eat in large groups. This too is an advantage over existing tablets or baits.

This form of the insecticide is effective for about one month and will need to be changed accordingly.

What is claimed is:

1. A composition for use as an insecticide, comprising boric acid and a bait that consists essentially of white wheat flour, solid white vegetable shortening, chopped onions, white cane sugar and water, wherein the ingredients of said composition are present in the relative proportion of 16 ounces of boric acid to 8 ounces of white wheat flour to 4 ounces of solid white vegetable shortening to 2 ounces of white cane sugar to 1 ounce of water and wherein said composition is in the form of flat patties.

2. The composition according to claim 1 wherein the dimensions of the patty are about 1½ inches in diameter and ½ inch in height.

3. A method for preparing a composition that is used as an insectcide, comprising the steps of:

mixing boric acid with a bait that consists essentially of white wheat flour, solid white vegetable shortening, chopped onins, white cane sugar and water, wherein said ingredients are mixed in relative proportions of 16 ounces of boric acid to 8 ounces of white wheat flour to 4 ounces of solid white vegetable shortening to 2 ounces of white cane sugar 1 ounce of water; and forming the resulting mixture into flat patties.

4. The method according to claim 3 wherein said patties are formed to a size of 1½ inches in diameter and about ½ in height.

* * * * *